(12) United States Patent
Ryat et al.

(10) Patent No.: US 6,356,085 B1
(45) Date of Patent: Mar. 12, 2002

(54) METHOD AND APPARATUS FOR CONVERTING CAPACITANCE TO VOLTAGE

(75) Inventors: Marc Ryat, Stockholm (SE); Dean Andersen, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 0 days.

(21) Appl. No.: 09/566,908

(22) Filed: May 9, 2000

(51) Int. Cl.[7] .......... G01R 27/26; G01R 27/02; G01R 22/00; G01N 25/56
(52) U.S. Cl. .......... 324/658; 324/671; 324/158.1; 324/607; 324/76.17; 73/514.32
(58) Field of Search .......... 324/658, 671, 324/158.1, 607, 76.17; 73/514.32

(56) References Cited

U.S. PATENT DOCUMENTS

| | | | |
|---|---|---|---|
| 5,281,921 A | * 1/1994 | Novak et al. | 324/671 |
| 5,473,257 A | * 12/1995 | Novak et al. | 324/671 |
| 5,530,342 A | * 6/1996 | Murphy | 324/158.1 |
| 5,621,399 A | * 4/1997 | Gruler | 340/870.37 |
| 5,808,198 A | * 9/1998 | Ward et al. | 73/514.32 |
| 6,300,776 B1 | * 10/2001 | Schreiber et al. | 324/607 |

* cited by examiner

*Primary Examiner*—Safet Metjahic
*Assistant Examiner*—Wasseem H. Hamdan
(74) *Attorney, Agent, or Firm*—Steven M. Mitchell

(57) ABSTRACT

An apparatus for converting capacitance in a capacitive sensor into a voltage signal. A capacitive sensor monitors a physical parameter. A capacitance of the sensor varies with the physical parameter. A voltage supply applies an alternating voltage to the capacitive sensor, which creates an output signal from the sensor. A modulator modulates the output signal, which produces a voltage signal that corresponds to the capacitance of the sensor.

32 Claims, 6 Drawing Sheets

METHOD AND APPARATUS FOR CONVERTING CAPACITANCE TO VOLTAGE

FIELD OF THE INVENTION

The present invention is directed to a method and apparatus for converting capacitance in a capacitive sensor to voltage.

BACKGROUND

In a capacitive sensor, the capacitance of one or more capacitors varies with variations of a physical parameter that is being monitored. Many different types of capacitive sensors are known, and many such sensors have been used to monitor and measure various types of physical parameters. An example of such a capacitive sensor is a microelectro mechanical system ("MEMS"), which may be used to sense acceleration. A typical MEMS sensor comprises one or more small capacitors etched into a piece of silicon. One plate of a MEMS capacitor is fixed and the other plate is moveable. Acceleration of the sensor causes the moveable plate to move, changing the capacitance of the capacitor. The amount of movement—and hence the change in capacitance—is proportional to the amount of acceleration.

Regardless of the type of capacitive sensor or the physical parameter being sensed, generally speaking, the variations in capacitance must be converted into a voltage signal before meaningful use can be made of the output of the sensor. The present invention is directed to a method and apparatus for converting capacitance into voltage. Although a MEMS sensor is mentioned above, the present invention is not limited to use with a MEMS sensor. Rather, the present invention may be used with any type of capacitive sensor.

SUMMARY OF THE INVENTION

The instant invention is directed to a method and apparatus for converting variations in capacitance in a capacitive sensor into a voltage signal. A capacitive sensor monitors a physical parameter, and a capacitance of the sensor varies with the physical parameter. An alternating voltage is applied to the capacitive sensor, which creates an output signal. The output signal is modulated to produce a voltage signal. The modulated signal is a voltage signal that corresponds to the capacitance of the sensor.

DETAILED DESCRIPTION OF THE PREFERRED EMBODIMENT

The present invention is directed to a method and apparatus for converting capacitance in a capacitive sensor into voltage. The following descriptions of preferred embodiments of the method and apparatus are intended to be exemplary only. The invention is not limited to the exemplary embodiments or the manner in which the exemplary embodiments operate or are described herein.

Figure 1:
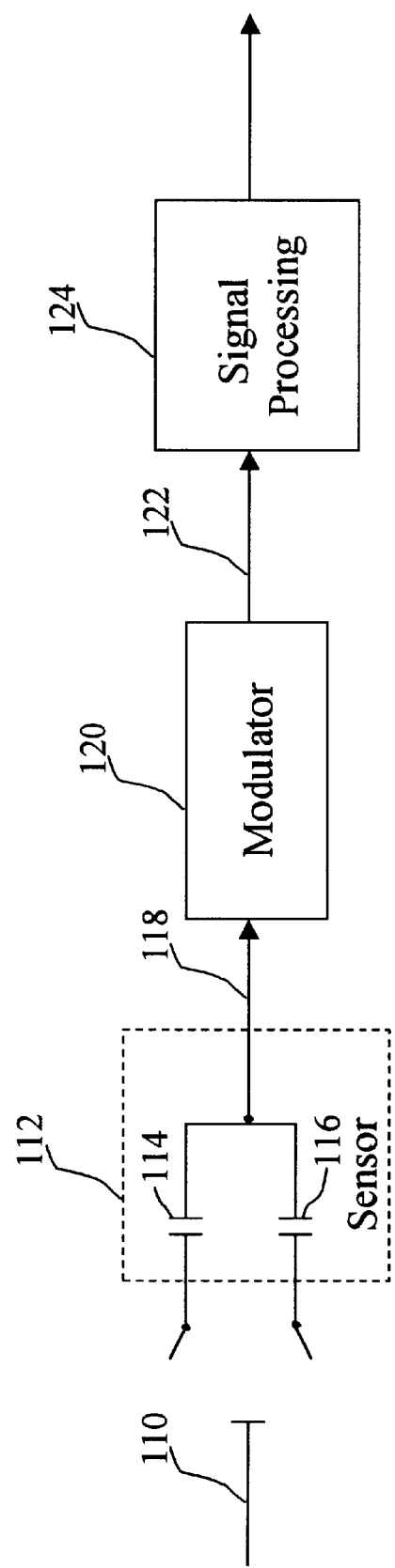
FIG. 1 is a block diagram of an exemplary circuit for converting capacitance to voltage.
Figure 2:
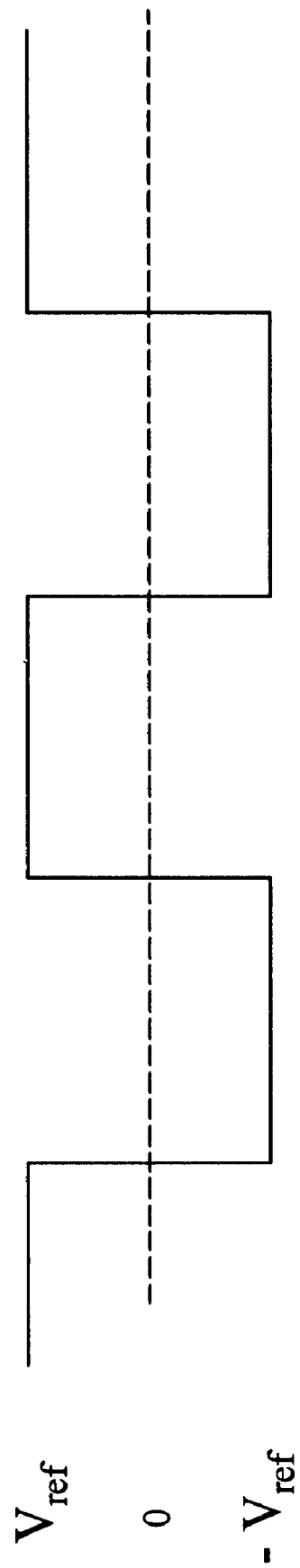
FIG. 2 illustrates an exemplary waveform applied to the sensor of FIG. 1.

FIG. 1 illustrates an exemplary capacitive sensor 112, a modulator 120, and a signal processing block 124. The modulator 120 may alternatively be a converter. The capacitive sensor 112 includes two capacitors 114, 116. The sensor is designed such that the capacitance of the two capacitors 114, 116 varies in accordance with a physical parameter that is being monitored by the sensor 112. Many different types and designs of capacitive sensors are known to those skilled in the art, and any such design may be used with the present invention. A periodic voltage waveform is switched between capacitors 114, 116 by switch 110. FIG. 2 illustrates an exemplary square waveform in which a reference voltage $V_{ref}$ is periodically applied to capacitor 114 and negative reference voltage $-V_{ref}$ is periodically applied to the other capacitor 116. The square waveform illustrated in FIG. 2 is exemplary only. Any other waveform shape can be used in place of the square wave shown in FIG. 2.

Applying the square wave of FIG. 2 to capacitors 114, 116 of sensor 112 causes a charge transfer at node 118 equal to the reference voltage $V_{ref}$ multiplied by the difference between the capacitance of capacitor 114 and the capacitance of capacitor 116. This is illustrated by the equation $Q=V_{ref}(C_1-C_2)$, where Q represents the charge transferred to node 118, $C_1$ represents the capacitance of capacitor 114, and $C_2$ represents the capacitance of capacitor 116. This signal is input into a modulator 120. The modulator 120 acts as an analog-to-digital converter. As described in more detail below, the modulator may comprise a sigma-delta modulator. As is known, a sigma-delta modulator converts an input signal into a serial bit stream whose downsampled value is a digital representation of the analog input of the modulator. As is also known, the pattern density of the digital output is proportional to the analog input. Thus, if modulator 120 is a sigma-delta modulator, the pattern density of output 122 is proportional to the difference in the capacitance of capacitors 114, 116. Output 122 thus carries a digital signal that represents the physical parameter being measured by sensor 112.

Typically, output 122 is further processed in order to extract useful information from the signal. This further processing is represented in FIG. 1 by signal processing block 124. Many methods and apparatuses for processing a sensor signal are known, and any such method or apparatus may be used with the present invention. Indeed, the processing method or apparatus used will typically depend on the type of physical parameter being monitored and the purpose of monitoring the parameter.

Figure 3:
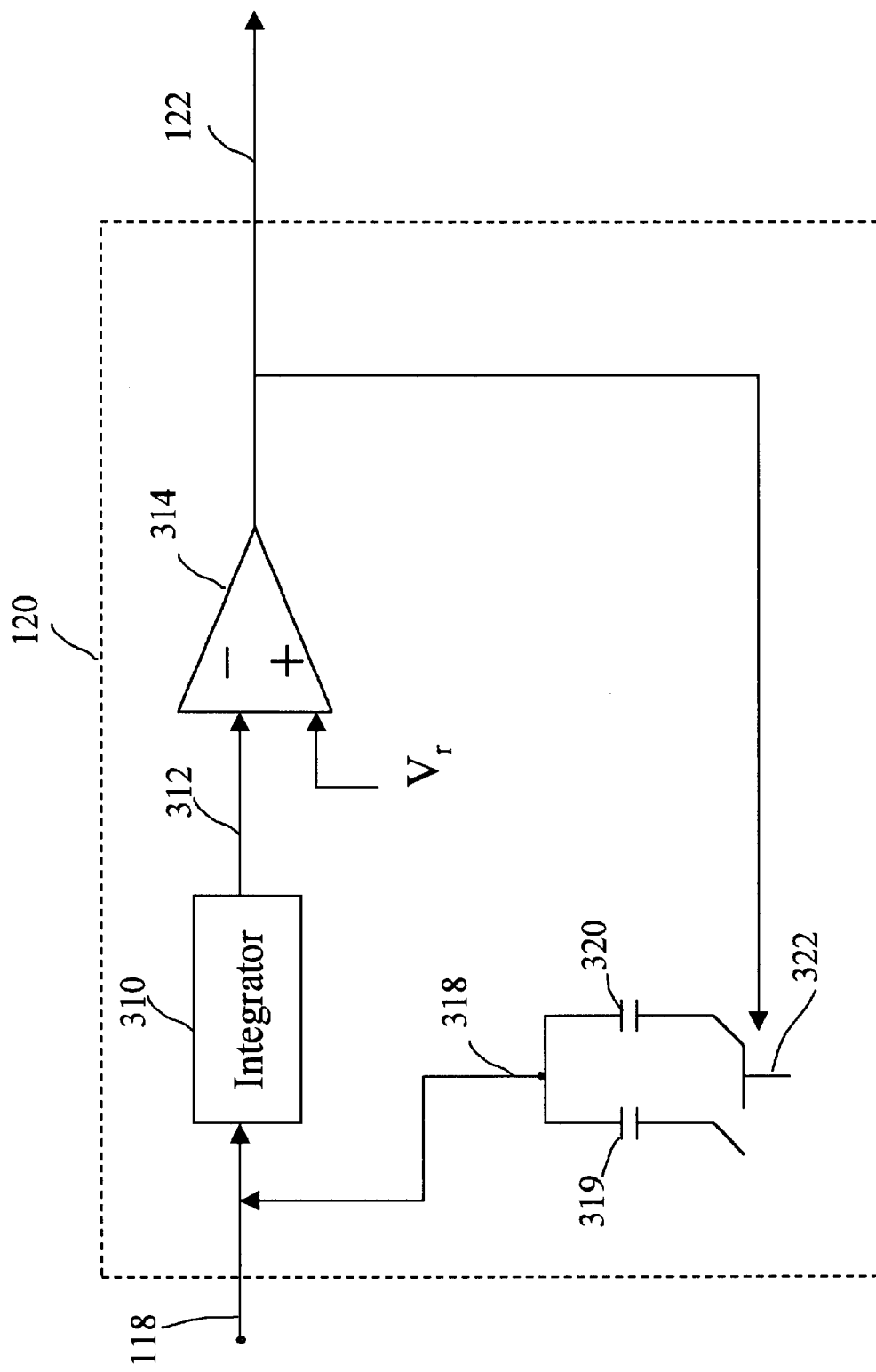
FIG. 3 is a block diagram of an exemplary embodiment of the modulator of FIG. 1.
Figure 5:
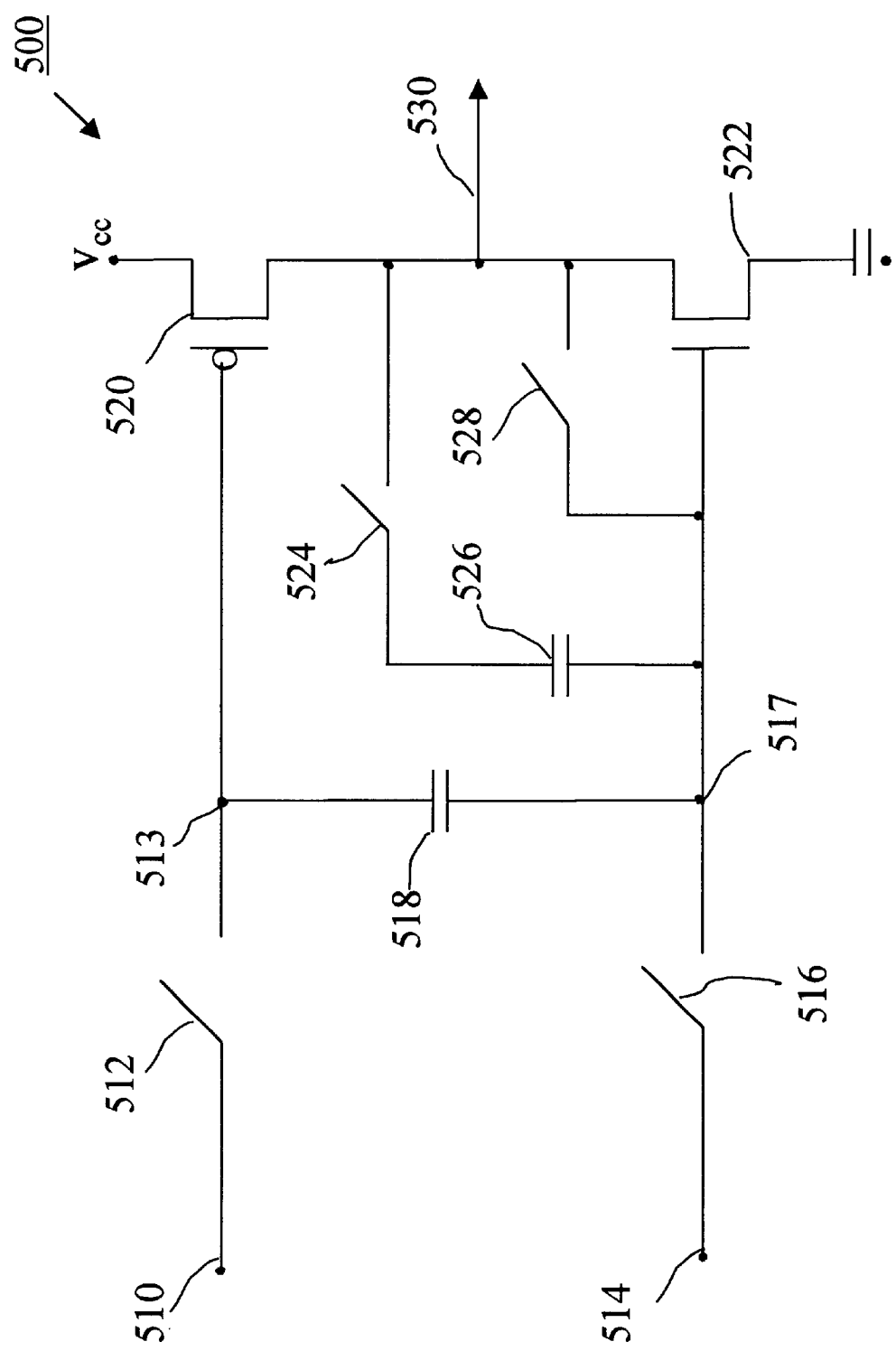
FIG. 5 illustrates an exemplary integrator that may be used with the present invention.

FIG. 3 illustrates an exemplary embodiment of modulator 120 of FIG. 1. The embodiment of the modulator 120 illustrated in FIG. 3 is a first order modulator that comprises an integrator 310, a comparator 314, feedback capacitors 319, 320, and switch 322. As the name implies, integrator 310 integrates node 118. A preferred integrator is illustrated in FIG. 5 and described in detail below. However, many integrator designs are known, and any such design can be used with the present invention. For example, the well know design in which the output of an operational amplifier is fed back through a capacitor to an input of the operational amplifier may be used rather than the integrator shown in FIG. 5. The output 312 of integrator 310 is input into a comparator 314, which quantizes the output 312 of the integrator 310. As shown in FIG. 3, input 312 is compared to a reference voltage $V_r$, which may be any suitable voltage, including zero volts.

The output 122 of the comparator 314 is a digital signal whose density is proportional to the difference in the capacitance of sensor capacitors 114, 116 of FIG. 1. The density level of output 122 thus represents the physical parameter being measured by sensor 112. The output 122 of the comparator 314 also controls switch 322. The nature of a comparator is such that output 122 is in one state while input 312 is greater than $V_r$ and in the other state while input 312 is less than $V_r$. Switch 322 is tied to a suitable voltage source (not shown) and configured such that capacitors 319, 320 feed a negative charge into node 118 while signal 122 is in one state. On the other hand, while signal 122 is in the other state, capacitors 319, 320 feed a positive charge into node 118. Preferably, capacitors 319 and 320 are sized such that every switching action of switch 322 injects a charge approximately equal to the full scale of the overall modulator 120. The particular sizes of capacitors 319 and 320 are not critical to the invention, however, and other sizes for these capacitors 319 and 320 may, be chosen. For example, the size of capacitors 319 and 320 may affect the gain and stability of modulator 120. The sizes of these capacitors may be chosen to achieve a desired gain and stability.

Figure 4:
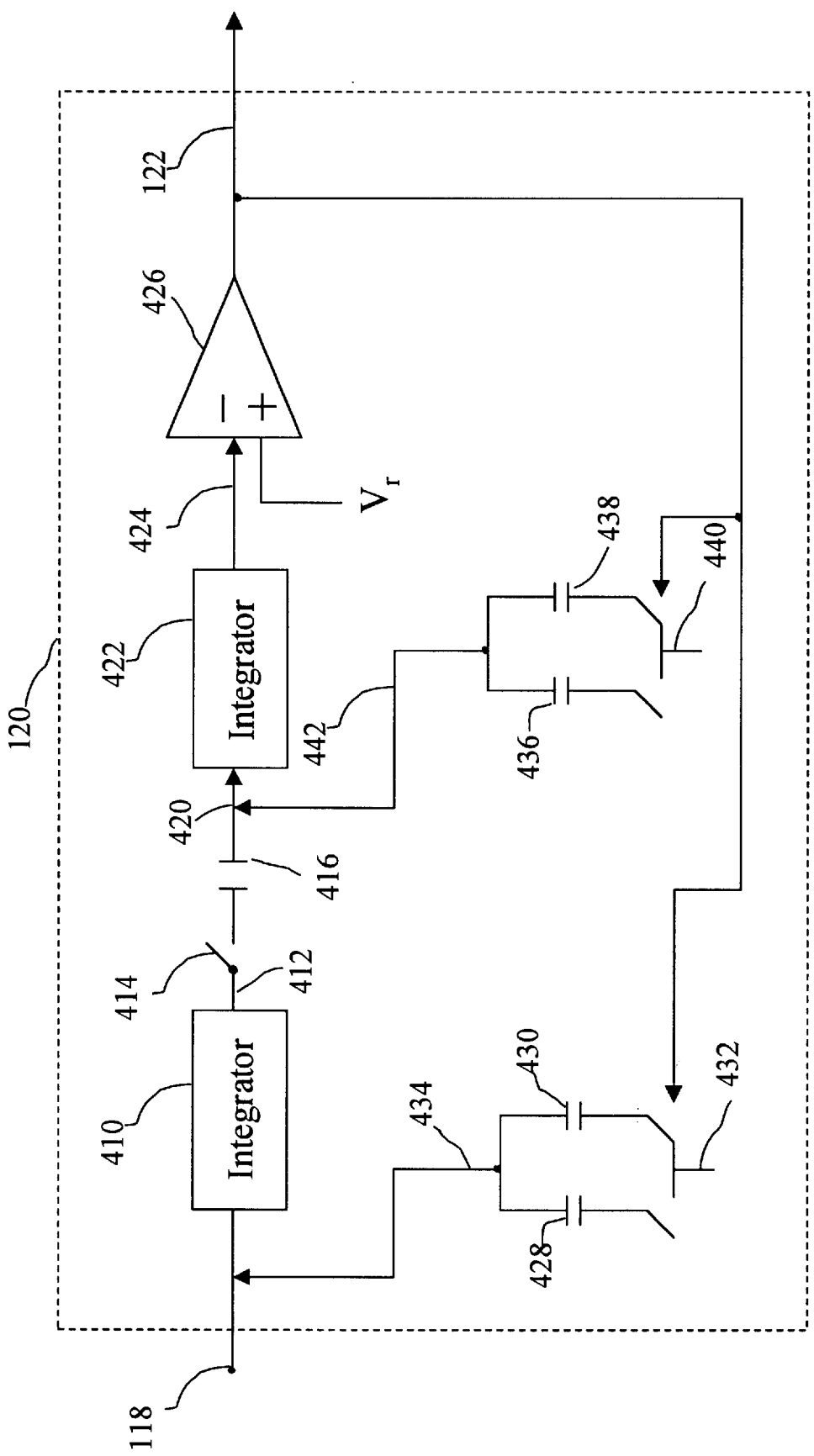
FIG. 4 is a block diagram of a second embodiment of the modulator of FIG. 1.

FIG. 4 illustrates a second exemplary embodiment of the modulator 120 of FIG. 1. The embodiment of the modulator 120 illustrated in FIG. 4 is a second order modulator. It includes an integrator 410 that integrates node 118. The output 412 of integrator 410 is input into capacitor 416 through switch 414. In a preferred embodiment, switch 414 is controlled by a suitable clock. The charge at node 420 of capacitor 416 is input into a second integrator 422. (Integrators 410 and 422 may be of the same general design as integrator 310 of FIG. 3.) The output 424 of integrator 422 is input into comparator 426, which quantizes the output 424 of integrator 422. (Comparator 426 may be similar to comparator 314 of FIG. 3.)

The output 122 of the comparator 426 is a digital signal that represents the difference in the capacitance of sensor capacitors 114, 116 of FIG. 1. The digital code of output 122 thus will represent, after decimation, the physical parameter being measured by sensor 112. Similar to comparator 314 of FIG. 3, the output 122 of comparator 426 is in one state while input 424 is greater than $V_r$ and in another state while input 424 is less than $V_r$. The output 122 of the comparator 426 controls switches 432 and 440. Like switch 322 of FIG. 3, switches 432 and 440 of FIG. 4 are tied to suitable voltage sources (not shown). Switch 432 is configured such that capacitors 428, 430 feed a negative charge into node 118 while signal 122 is in one state; while signal 122 is in the other state, capacitors 428, 430 feed a positive charge into node 118. Similarly, switch 440 is configured such that capacitors 436, 438 feed a negative charge into node 420 while signal 122 is in one state; on the other hand, while signal 122 is in the other, capacitors 436, 438 feed a positive charge into node 420.

FIG. 5 illustrates an exemplary embodiment of an integrator 500 that may be used in the circuits illustrated in FIGS. 3 and 4. Input 510 (not shown in FIGS. 3 or 4) is connected to a bias voltage. Preferably, the bias voltage is provided by a PMOS transistor (not shown) connected as a diode into which a fixed current source (not shown) is injected. Input 514 is connected to the output of a capacitor whose stored charge is to be integrated by the integrator of FIG. 5. Thus, input 514 corresponds to node 118 in FIG. 3 and nodes 118 and 420 in FIG. 4. Capacitor 518 maintains a voltage difference between nodes 513 and 517. Capacitor 526 is the integrating capacitor. Switches 512, 516, 524, and 528 are controlled by a clock signal and cause the integrator 500 to operate in two periodically changing modes: auto zero mode and integration mode.

In essence, the auto zero mode resets the integrator 500. Switches 512 and 528 are closed, and switches 516 and 526 are open. This refreshes the voltage difference between nodes 513 and 517 and shorts the integrating capacitor 526. During integration mode, switches 516 and 524 are closed and switches 512 and 528 are open. This connects input 514 to the output of the capacitor whose stored charge is to be integrated (e.g., capacitors 114 and 116 of FIG. 1 or capacitor 416 of FIG. 4) and enables the integrating capacitor 526. Transistors 520 and 522 form an inverting amplifier and may be complementary metal oxide semiconductor ("CMOS") transistors. While switches 516 and 524 are closed, the charge Q transferred into node 517 is equal to the charge injected by the capacitor whose output is connected to input 514. Preferably, switches 512, 516, 524, and 528 are controlled by a digital clock such that the integrator 500 is put in auto zero mode during one phase of the clock and integration mode during another phase of the clock.

Figure 6:
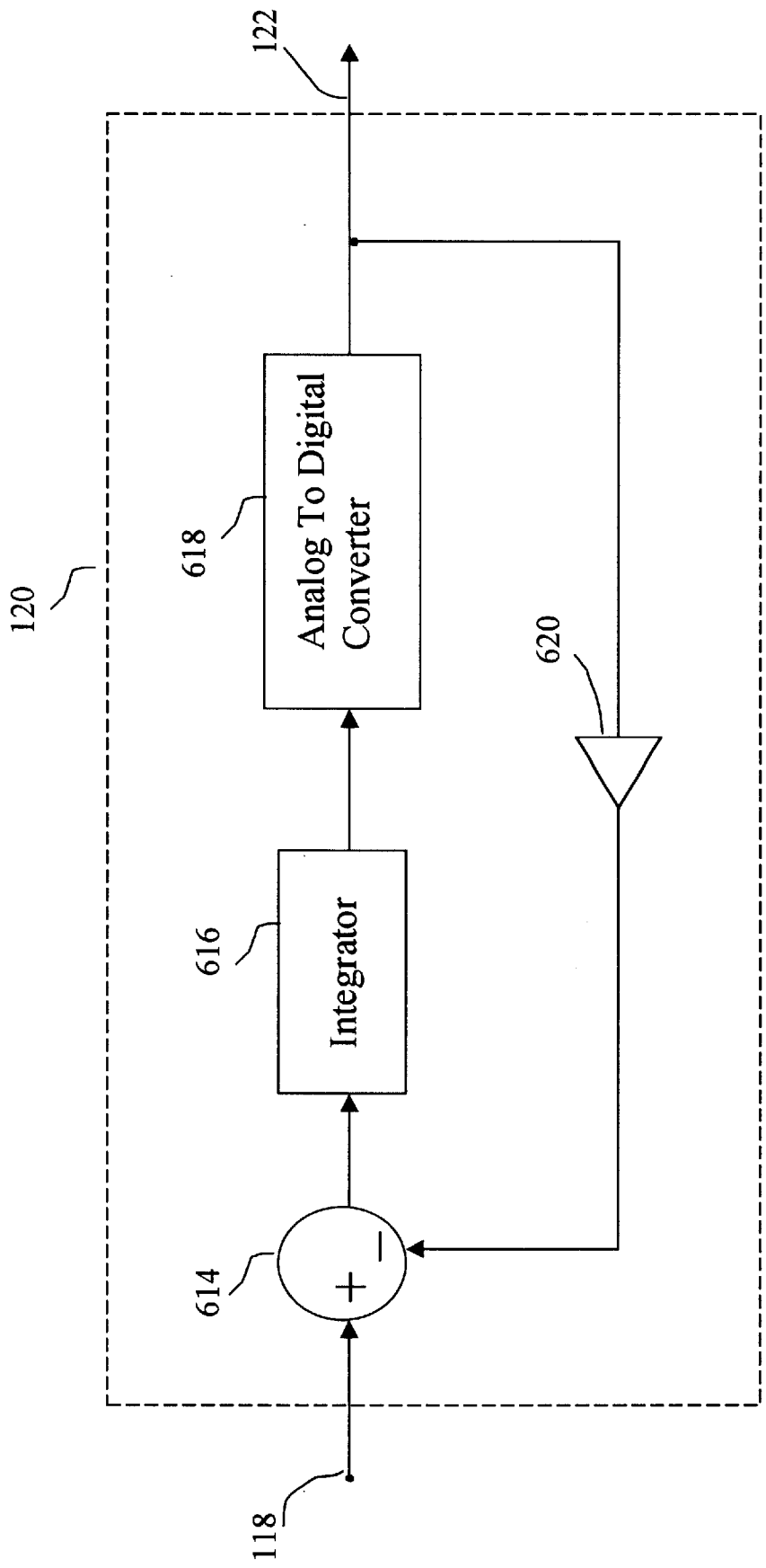
FIG. 6 illustrates an alternative embodiment of the modulator of FIG. 1.

The above described embodiments of the invention are not intended to be limiting. Persons skilled in the art will appreciate that modifications may be made to the these embodiments and alternative embodiments may be created that are within the scope and spirit of the invention. For example, any sigma-delta converter may be used as the modulator 120 of FIG. 1, including the first order sigma-delta converter illustrated in FIG. 6 or a sigma-delta converter of any higher order. As shown in FIG. 6, a subtractor 614 subtracts a feedback signal from node 118. The output of the subtractor 614 is integrated by integrator 616 and then converted into digital format by analog to digital converter 618. The output of the analog to digital converter 618 is amplified by amplifier 620, which outputs the feedback signal.

What is claimed is:

1. An apparatus comprising:
 a capacitive sensor;
 a voltage supply configured to apply a voltage to said capacitive sensor, thereby producing a sensor output signal; and
 a modulator configured to receive as an input said sensor output signal, wherein said modulator comprises:
  a first integrator configured such that an input of said first integrator is electrically responsive to said sensor output signal;
  a second integrator configured such that an input of said second integrator is electrically responsive to an output of said first integrator;
  a comparator configured such that an input of said comparator is electrically responsive to an output of said second integrator.

2. The apparatus of claim 1, wherein said voltage applied to said capacitive sensor comprises a periodically alternating voltage.

3. The apparatus of claim 1, wherein said modulator comprises a first order modulator.

4. The apparatus of claim 1, wherein said modulator comprises:
 an integrator configured such that an input of said integrator is electrically responsive to said sensor output signal; and
 a comparator configured such that an input of said comparator is electrically responsive to an output of said integrator.

5. The apparatus of claim 4, wherein said modulator further comprises at least one feedback capacitor that is electrically connected to an input of said integrator.

6. The apparatus of claim 4, wherein said modulator further comprises at least two feedback capacitors that are electrically connected to an input of said integrator, and an output of said comparator controls said feedback capacitors.

7. The apparatus of claim 1, wherein said modulator comprises a second order modulator.

8. The apparatus of claim 1, wherein said modulator further comprises:
  at least one first feedback capacitor that is electrically connected to an input of said first integrator; and
  at least one second feedback capacitor that is electrically connected to an input of said second integrator.

9. The apparatus of claim 1, wherein said modulator further comprises
  a first set of at least two feedback capacitors that are electrically connected to an input of said first integrator; and
  a second set of at least two feedback capacitors that are electrically connected to an input of said second integrator.

10. The apparatus of claim 9, wherein an output of said comparator controls said first set of at least two feedback capacitors.

11. The apparatus of claim 9, wherein an output of said comparator controls said second set of at least two feedback capacitors.

12. The apparatus of claim 1, wherein said capacitive sensor comprises at least two capacitors.

13. The apparatus of claim 12, wherein said voltage supply periodically applies said voltage first to a first plate of one of said at least two capacitors and then to a first plate of another of said at least two capacitors.

14. The apparatus of claim 13, wherein a second plate of said one of said at least two capacitors is electrically connected to a second plate of said other of said at least two capacitors.

15. The apparatus of claim 1, in which said modulator comprises at least one integrator.

16. The apparatus of claim 15, wherein said at least on integrator comprises a single-ended amplifier.

17. The apparatus of claim 15, wherein said at least one integrator comprises at least one switch for placing the integrator into an integration mode.

18. The apparatus of claim 17, wherein said at least one integrator comprises at least one additional switch for placing the integrator into a reset mode.

19. The apparatus of claim 18, wherein a periodic digital clock controls said at least one switch and said at least one additional switch.

20. An apparatus comprising:
  capacitive sensor means for monitoring a physical parameter;
  voltage supply means for applying a voltage to said capacitive sensor, thereby producing a sensor output signal; and
  modulating means for modulating said sensor output signal, wherein said modulating means comprises:
    first integrating means for integrating said sensor output signal;
    second integrating means for integrating an output of said first integrating means; and
    comparing means for comparing an output of said second integrating means to a reference signal.

21. The apparatus of claim 20 wherein said voltage applied to said capacitive sensor means comprises a periodically alternating voltage.

22. The apparatus of claim 20, wherein said modulating means comprises:
  integrating means for integrating said sensor output signal; and
  comparing means for comparing an output of said integrating means to a reference signal.

23. The apparatus of claim 22, wherein said modulating means further comprises feedback means for feeding a signal into an input of said integrating means.

24. The apparatus of claim 23, wherein an output of said comparing means controls said feedback means.

25. The apparatus of claim 21, wherein said modulating means further comprises:
  first feedback means for feeding a first signal into an input of said first integrating means; and
  second feedback means for feeding a second signal into an input of said second integrating means.

26. The apparatus of claim 25, wherein an output of said comparing means controls said first feedback means and said second feedback means.

27. A method comprising:
  applying a voltage to a capacitive sensor, thereby producing a sensor output signal; and
  modulating said sensor output signal, wherein the step of modulating said sensor output signal comprises:
    integrating said sensor output signal, thereby producing a first integrated signal;
    integrating said first integrated signal, thereby producing a second integrated signal; and
    comparing said second integrated signal to a reference signal, thereby producing a comparator output signal.

28. The method of claim 27, wherein said voltage applied to said capacitive sensor comprises a periodically alternating voltage.

29. The method of claim 27, wherein the step of modulating said sensor output signal comprises:
  integrating said sensor output signal, thereby producing an integrated signal; and
  comparing said integrated signal to a reference signal, thereby producing a comparator output signal.

30. The method of claim 29, wherein the step of modulating said sensor output signal further comprises controlling a feedback signal in accordance with said comparator output signal.

31. The method of claim 29, wherein the step of modulating said sensor output signal further comprises controlling feedback signals in accordance with said comparator output signal.

32. The method of claim 27 further including switching between a modulating mode and a reset mode.

* * * * *